(12) United States Patent
Gu et al.

(10) Patent No.: US 11,136,616 B2
(45) Date of Patent: Oct. 5, 2021

(54) OLIGONUCLEOTIDES AND METHODS FOR THE PREPARATION OF RNA LIBRARIES

(71) Applicant: LIFE TECHNOLOGIES CORPORATION, Carlsbad, CA (US)

(72) Inventors: Jian Gu, Austin, TX (US); Kelli Bramlett, Austin, TX (US); Christopher Burnett, Austin, TX (US)

(73) Assignee: Life Technologies Corporation, Carlsbad, CA (US)

( * ) Notice: Subject to any disclaimer, the term of this patent is extended or adjusted under 35 U.S.C. 154(b) by 433 days.

(21) Appl. No.: 15/950,921

(22) Filed: Apr. 11, 2018

(65) Prior Publication Data

US 2018/0230516 A1    Aug. 16, 2018

Related U.S. Application Data

(62) Division of application No. 13/774,648, filed on Feb. 22, 2013, now Pat. No. 9,970,048.

(60) Provisional application No. 61/624,940, filed on Apr. 16, 2012.

(51) Int. Cl.
*C12Q 1/68* (2018.01)
*C12Q 1/6806* (2018.01)
*C12Q 1/6848* (2018.01)

(52) U.S. Cl.
CPC ......... *C12Q 1/6806* (2013.01); *C12Q 1/6848* (2013.01)

(58) Field of Classification Search
CPC ............................ C12Q 1/6848; C12Q 1/6806
See application file for complete search history.

(56) References Cited

U.S. PATENT DOCUMENTS

| | | | |
|---|---|---|---|
| 5,567,583 | A | 10/1996 | Wang et al. |
| 5,849,497 | A | 12/1998 | Steinman |
| 6,130,038 | A | 10/2000 | Becker et al. |
| 6,391,592 | B1 | 5/2002 | Su et al. |
| 7,700,287 | B2 | 4/2010 | Chen |
| 9,970,048 | B2 | 5/2018 | Gu et al. |
| 2003/0211483 | A1* | 11/2003 | Schroeder ............ C12Q 1/686 435/6.12 |
| 2006/0281092 | A1* | 12/2006 | Wille .................... C12Q 1/6809 435/6.11 |
| 2009/0130720 | A1 | 5/2009 | Nelson et al. |
| 2010/0233699 | A1 | 9/2010 | Nazarenko et al. |
| 2010/0279305 | A1 | 11/2010 | Kuersten |
| 2010/0285478 | A1 | 11/2010 | Chen et al. |
| 2011/0104785 | A1 | 5/2011 | Vaidyanathan et al. |
| 2012/0295794 | A1 | 11/2012 | Kuersten |
| 2013/0261027 | A1* | 10/2013 | Li ........................ C12N 9/1252 506/26 |

FOREIGN PATENT DOCUMENTS

| | | |
|---|---|---|
| EP | 2240606 A1 | 10/2010 |
| EP | 2240606 B1 | 10/2016 |
| EP | 2839024 B1 | 9/2017 |
| EP | 3301188 A1 | 4/2018 |
| WO | 01/90415 A2 | 11/2001 |
| WO | 2009/091719 A1 | 7/2009 |
| WO | 2012/033687 A1 | 3/2012 |
| WO | 2012/044847 | 4/2012 |

OTHER PUBLICATIONS

Kawano M, Kawazu C, Lizio M, et al. Reduction of non-insert sequence reads by dimer eliminator LNA oligonucleotide for small RNA deep sequencing. Biotechniques. 2010; 49(4):751-755. (Year: 2010).*
Watkins NE Jr, SantaLucia J Jr. Nearest-neighbor thermodynamics of deoxyinosine pairs in DNA duplexes. Nucleic Acids Res. Nov. 1, 2005; 33(19):6258-67. (Year: 2005).*
**Chun, Jong-Yoon, et al., "Dual priming oligonucleotide system for the multiplex detection of respiratory viruses and SNP genotyping of CYP2C19 gene", Nucleic Acids Res., 35(6):e40, 2007, 1-6.
Gregoire, et al., "Amplification of human papillomavirus DNA sequences by using conserved primers.", Journal of Clinical Microbiology, 1989, 2660-2665.
**Kawano, Mitsuoki, et al., "Reduction of non-insert sequence reads by dimer eliminator LNA oligonucleotide for small RNAdeep sequencing", BioTechniques, 49(4), 2010, 751-755.
**Loakes, "Survey and Summary: The applications of universal DNA base analogues", Nucleic Acids Research, Jun. 2001, 29(12):2437-2447.
**Majlessl, M., et al., "Advantages of 2'-O-methyl oligoribonucleotide probes for detecting RNA targets", Nucleic Acids Research; vol. 26(9), 1988, 2224-2229.
**Martin, FH, et al., "Base Pairing Involving Deoxyinosine: Implications for Probe Design", Nucl. Acids. Res., 1985, 13:24, 8927-8938.
**PCT/US2013/027423 , International Search Report dated Jul. 16, 2013, 5 pages.
**Tsourkas, A., et al., "Hybridization of 2'-O'methyl and 2'-deoxy molecular beacons to RNA and DNA targets", Nucleic Acids Research, Dec. 1, 2002, 30(23):5168-5174.
**Watkins, N. E., et al., "Nearest-neighbor thermodynamics of deoxyinosine pairs in DNA duplexes", Nucleic Acids Research, Nov. 1, 2005, 33(19):6258-6267.

(Continued)

*Primary Examiner* — Teresa E Strzelecka
*Assistant Examiner* — Olayinka A Oyeyemi

(57) ABSTRACT

Disclosed are compositions and methods for the preparation of RNA libraries for sequencing, gene expression profiling, microarray and other uses and for simplification of the library preparation process. The disclosure provides blocking oligonucleotides which bind to byproduct nucleic acid molecules formed during the ligation of adapters to nucleic acid segments prior to sequencing and inhibit or block amplification of the byproduct nucleic acid molecules in subsequent amplification reactions. Methods for library preparation using blocking oligonucleotides are also provided.

18 Claims, 9 Drawing Sheets

Specification includes a Sequence Listing.

(56) References Cited

OTHER PUBLICATIONS

Beaucage S.L., et al., "The Synthesis of Modified Oligonucleotides by the Phosphoramidite Approach and Their Applications" Tetrahedron 49(28), 1993, pp. 6123-6194.
Eddy S.R., "Non-Coding RNA Genera and The Modern RNA World", Nature Reviews Genetics, vol. 2, Dec. 1, 2001, pp. 919-929.
Extended European Search Report for Application No. 17189306.8, dated Feb. 15, 2018, 9 pages.
Gaubert G., et al., "Synthesis of 1-(2'-O-Methyl-β-d-Ribofuranosyl)-5-Nitroindole and its Phosphoramidite Derivative," Tetrahedron Letters, vol. 45, No. 29, Jul. 12, 2004, pp. 5629-5632.
Hannon G.J., et al., "The Expanding Universe of Noncoding RNAs", Cold Spring Harbor Symposia on Quantitative Biology, vol. LXXI, 2006, pp. 551-564.
Mattick et al., "Non-coding RNA", Human Molecular Genetics, vol. 15, Review Issue 1, 2006, pp. R17-R29.

\* cited by examiner

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cctgcgtgtc tccgactcag                                              20

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other

<400> SEQUENCE: 2
nnnnnnctga gtcggagaca cgcagg                                       26

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atcaccgact gcccatagag agg                                          23

<210> SEQ ID NO 4
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (11)..(16)
<223> OTHER INFORMATION: a, c, t, g, unknown or other

<400> SEQUENCE: 4
agtcggtgat nnnnnn                                                        16

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(24)
<223> OTHER INFORMATION: di-deoxy-C

<400> SEQUENCE: 5
atcaccgact gcccatagag aggc                                               24

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cctctctatg ggcagtcg                                                      18

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcagtcggtg atctgagtcg gaga                                               24

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccgctttcct ctctatgggc agtcggtgat                                         30

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggccaaggcg                                                               10
```

```
<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other

<400> SEQUENCE: 10
nnnnnncgcc ttggcc                                                      16

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(13)
<223> OTHER INFORMATION: 2'-O-methyl modified nucleotides
<220> FEATURE:
<221> NAME/KEY: modified_base
<222> LOCATION: (14)..(14)
<223> OTHER INFORMATION: Inosine
<220> FEATURE:
<221> NAME/KEY: modified_base
<222> LOCATION: (17)..(17)
<223> OTHER INFORMATION: 2'-O-methyl modified nucleotides
<220> FEATURE:
<221> NAME/KEY: modified_base
<222> LOCATION: (18)..(18)
<223> OTHER INFORMATION: Inosine
<220> FEATURE:
<221> NAME/KEY: modified_base
<222> LOCATION: (19)..(26)
<223> OTHER INFORMATION: 2'-O-methyl modified nucleotides
<220> FEATURE:
<223> OTHER INFORMATION: 3' amine

<400> SEQUENCE: 11
atgggcagtc ggtnatcncc ttggcc                                           26

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccatctcatc cctgcgtgtc tccgactcag ggccaaggcg                            40

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gcagtcggtg atcgccttgg cc                                               22
```

```
<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccatctcatc cctgcgtgtc tccgactcag                                        30
```

OLIGONUCLEOTIDES AND METHODS FOR THE PREPARATION OF RNA LIBRARIES

CROSS REFERENCE TO RELATED APPLICATIONS

This application is a Divisional application of U.S. Ser. No. 13/774,648, filed Feb. 22, 2013, which claims the benefit of priority under 35 U.S.C. § 119(e) to U.S. Provisional Application No. 61/624,940 filed Apr. 16, 2012, the disclosures of which are all incorporated herein by reference in their entireties.

SEQUENCE LISTING

The instant application contains a Sequence Listing which has been submitted in ASCII format via EFS-Web and is hereby incorporated by reference in its entirety. Said ASII copy, created on May 3, 2013, is named LT00678_SL.txt and is 4,309 bytes in size.

FIELD

The disclosure generally relates to methods and compositions for the preparation of RNA libraries for sequencing, gene expression profiling, microarrays and other techniques and for simplification of the library preparation process.

BACKGROUND

Analysis of genome expression patterns provides valuable insight into the role of differential expression in a wide variety of biological processes, including but not limited to, various disease states. Such analysis, whether mRNA-based gene expression or small non-coding RNA-based expression analysis, is becoming a rapidly expanding avenue of investigation in many disciplines in the biological sciences. Small non-coding RNA discovery is also an area of great scientific and medical interest. It is believed that by knowing what parts of the genome are transcribed when and why, a better understanding of many complex and inter-related biological processes may be obtained.

Small non-coding RNAs are rapidly emerging as significant effectors of gene regulation in a multitude of organisms spanning the evolutionary spectrum. Animals, plants and fungi contain several distinct classes of small RNAs; including without limitation, miRNAs, siRNAs, piRNAs, and rasiRNAs. These small gene expression modulators typically fall within the size range of .about.18-40 nt in length, however their effect on cellular processes is profound. They have been shown to play critical roles in developmental timing and cell fate mechanisms, tumor progression, neurogenesis, transposon silencing, viral defense and many more. They function in gene regulation by binding to their targets and negatively effecting gene expression by a variety of mechanisms including heterochromatin modification, translational inhibition, mRNA decay and even nascent peptide turnover mechanisms. Therefore, identification of small RNAs in a given sample can greatly facilitate gene expression analysis.

Some small RNAs are produced from defined locations within the genome. MicroRNAs are such a class; they are typically transcribed by RNA polymerase II from polycistronic gene clusters or can also be generated from pre-mRNA introns. Thus far several thousand unique miRNA sequences are known. Other classes of small RNAs, such as piRNAs or endogenous siRNA, are not typically transcribed from a defined locus in the genome. Instead, they are generated in response to events such as viral infections or retrotransposon expression and serve to silence these 'foreign' sequences that would otherwise result in serious detriment to the cell. Descriptions of ncRNA can be found in, among other places, Eddy, Nat. Rev. Genet. 2:919-29, 2001; Mattick and Makunin, Human Mol. Genet. 15:R17-29, 2006; Hannon et al., Cold Springs Harbor Sympos. Quant. Biol. LXXI:551-64, 2006. Sequencing the entire population of small RNAs in a sample provides a direct method to identify and even profile all classes of these RNAs at one time.

Sequencing of nucleic acid molecules including small RNA molecules generally involves production of libraries of nucleic acid segments to which adapter sequences are added to each end. Sequencing of RNA typically involves a reverse transcription step to produce a cDNA molecule for sequencing. A major by-product when adding adapters to nucleic acids in preparing RNA sequencing libraries is an adapter: adapter product. This undesired by-product is generated when a 5' adaptor is ligated directly to a 3' adaptor with no RNA insert in between. These byproducts can occur when either single or double stranded adapters are used and when the 5' and 3' adapters are ligated simultaneously or sequentially. This by-product may be formed at a higher rate with library preparation methods which include denaturation directly after ligation and use an exogenous reverse transcriptase primer added prior to the reverse transcription reaction. Thus, the cDNA that is generated from the reverse transcription reaction contains both the intended library inserts and the undesired by-product. In order to remove the undesired by-product a gel purification step may be needed to remove the adaptor:adaptor by-product prior to subsequent PCR amplification reactions. If the adaptor:adaptor by-product is not minimized or removed, much of the PCR amplification components may be preferentially utilized to amplify the by-product instead of the library inserts of interest. Thus sequencing capacity and reagents will be spent on sequencing this byproduct thereby limiting the yield of the RNA segment of interest. Purification of the ligation reaction to remove byproducts is a cumbersome step for customers and eliminates the possibility of using automated library preparation procedures.

SUMMARY

In order to simplify the process of library preparation for RNA sequencing, gene expression profiling, microarray and other applications we have designed a single stranded blocking oligonucleotide which is able to specifically bind to an adaptor:adaptor by-product formed during ligation reactions performed in the process of library preparation prior to sequencing. Ligation reactions are used in the process of library creation to add sequencing adapters to the ends of the nucleic acid segment to be sequenced. The blocking oligonucleotide, when forming a duplex with a ligation byproduct, may be able to interfere with the ability of the reverse transcription primer to bind to the 3' adapter or with the ability of the reverse transcriptase to extend the template so that the byproduct is not transcribed and amplified in subsequent amplification reactions. Use of the blocking oligonucleotide allows for elimination of a purification step and thereby provides a simpler and potentially more automated library preparation process.

A blocking oligonucleotide may comprise an oligonucleotide comprising a first segment at a 5' prime end and a second segment at a 3' end, wherein the first segment hybridizes with a first nucleotide adapter molecule and the second segment hybridizes with a second nucleotide adapter molecule. In some embodiments the blocking oligonucleotide may be from 20 to 26 nucleotides in length. In other embodiments the blocking oligonucleotide may be 20, 21, 22, 23, 24, 25 or 26 nucleotides in length.

In some embodiments, the blocking oligonucleotide may comprise a first segment at a 5' end which may hybridize with a first nucleic acid adaptor. The first segment may be 11, 12, 13 or 14 nucleotides in length. In some embodiments the first segment may comprise from 1 to 14 modified nucleic acids. In certain embodiments the first segment may comprise 1, 2, 3, 4, 5, 6, 7, 8, 9, 10, 11, 12, 13 or 14 modified nucleotides. In some embodiments, the from 1 to 14 modified nucleic acids are located sequentially at the 5' end of the first segment. In other embodiments, the modified nucleic acids may be at any location within the first segment. The modified nucleic acids may include but are not limited to 2'-O-methyl modified nucleotides and locked nucleic acids (LNA).

In some embodiments, normal nucleotides which may be present in the first segment may be substituted with from 1-5 indiscriminate nucleotides. Indiscriminate nucleotides include inosine. In further embodiments, the indiscriminate nucleotides may be present at any position within the last 7 nucleotides at the 3' end of the first segment.

In further embodiments, the blocking oligonucleotide may comprise a second segment at a 3' end which may hybridize with a second nucleic acid adaptor. The second segment may be 9, 10, 11 or 12 nucleotides in length. In other embodiments the second segment may comprise one or more modified nucleic acids. In some embodiments all of the second segment nucleotides may be modified. Suitable modified nucleic acids include, but are not limited to 2'-O-methyl modified nucleotides and LNA. The second segment may further comprise an amine or other blocking group at its 3' end.

In some embodiments, normal and/or modified nucleotides which may be present in the second segment may be substituted with from 1-5 indiscriminate nucleotides. Indiscriminate nucleotides include inosine. In further embodiments, the indiscriminate nucleotides may be present at any position within the first 7 nucleotides at the 5' end of the second segment.

Further embodiments include methods for adding adapters to the ends of a plurality of a single stranded oligonucleotides comprising: a) forming a mixture of the single stranded oligonucleotides with a double stranded 5' adapter and a double stranded 3' adapter, b) adding an RNA ligase to the mixture under conditions such that the 5' adapter and the 3' adapter are ligated to the ends of the plurality of single stranded oligonucleotides, c) denaturing oligonucleotides present in step (b) and adding a blocking oligonucleotide under conditions such that the blocking oligonucleotide binds to an artifact of the ligation reaction formed when the 5' adapter and the 3' adapter are ligated to each other, such that reverse transcription of the artifact is inhibited or blocked.

DETAILED DESCRIPTION

Presented here are compositions and methods for preparing single stranded blocking oligonucleotides which are able to specifically bind to adapter:adapter byproducts formed during the process of adapter ligation of RNA molecules in preparation for sequencing, gene expression analysis, microarrays or other uses. Use of blocking oligonucleotides simplifies the process of RNA library preparation. The blocking oligonucleotide is able to block the activity of reverse transcriptase so that the byproduct is not transcribed and amplified in subsequent amplification reactions prior to sequencing. Use of the blocking oligonucleotide allows for elimination of a purification step and thereby provides a simpler and potentially more automated library preparation process.

Definitions

In the description that follows, a number of terms related to recombinant DNA technology are used. In order to provide a clear and consistent understanding of the specification and claims, including the scope to be given such terms, the following definitions are provided.

Adapter: is a nucleotide sequence added to the 5' or 3' end of a nucleic acid segment to be sequenced. Adapters provide priming sequences that are used for both amplification and sequencing of the nucleic acid segment. Adapters may also contain other sequences such as barcode sequences that are useful for sequencing or other applications.

Byproduct: is a product nucleic acid molecule which is formed by the unintended joining of two or more nucleic acid molecules or a product nucleic molecule in which not all of the intended joining events have occurred during a reaction in which multiple nucleic acid molecules are present.

Normal nucleotide: is a nucleotide comprising one of the naturally occurring bases adenine, guanine, thymine, cytosine or uracil.

Modified nucleotide: is a nucleotide where either or both of the purine or pyrimidine base or the sugar have been modified. Non-limiting examples of modified nucleotides include 2'-O-methyl modified nucleotides, 2'-deoxy-2'-fluoro modified nucleotide, a 2'-deoxy-modified nucleotide, 2'-alkyl-modified nucleotides, locked nucleotides (LNA), nucleotides comprising a 5'-phosphorothioate group, a basic nucleotides, 2'-amino-modified nucleotides, morpholino nucleotides, phosphoramidates, and non-natural base comprising nucleotides.

Indiscriminant base: is a base that is capable of forming a Watson-Crick base pair with more than one other base. Examples of indiscriminant bases include 2'-deoxyinosine and derivatives thereof, nitrosolic analogues and hydrophobic aromatic non-hydrogen bonding bases.

Off-target: refers to any instance in which a nucleotide sequence hybridizes or partially hybridizes with another nucleic acid sequence wherein there is not perfect homology between the two sequences.

Figure 1:
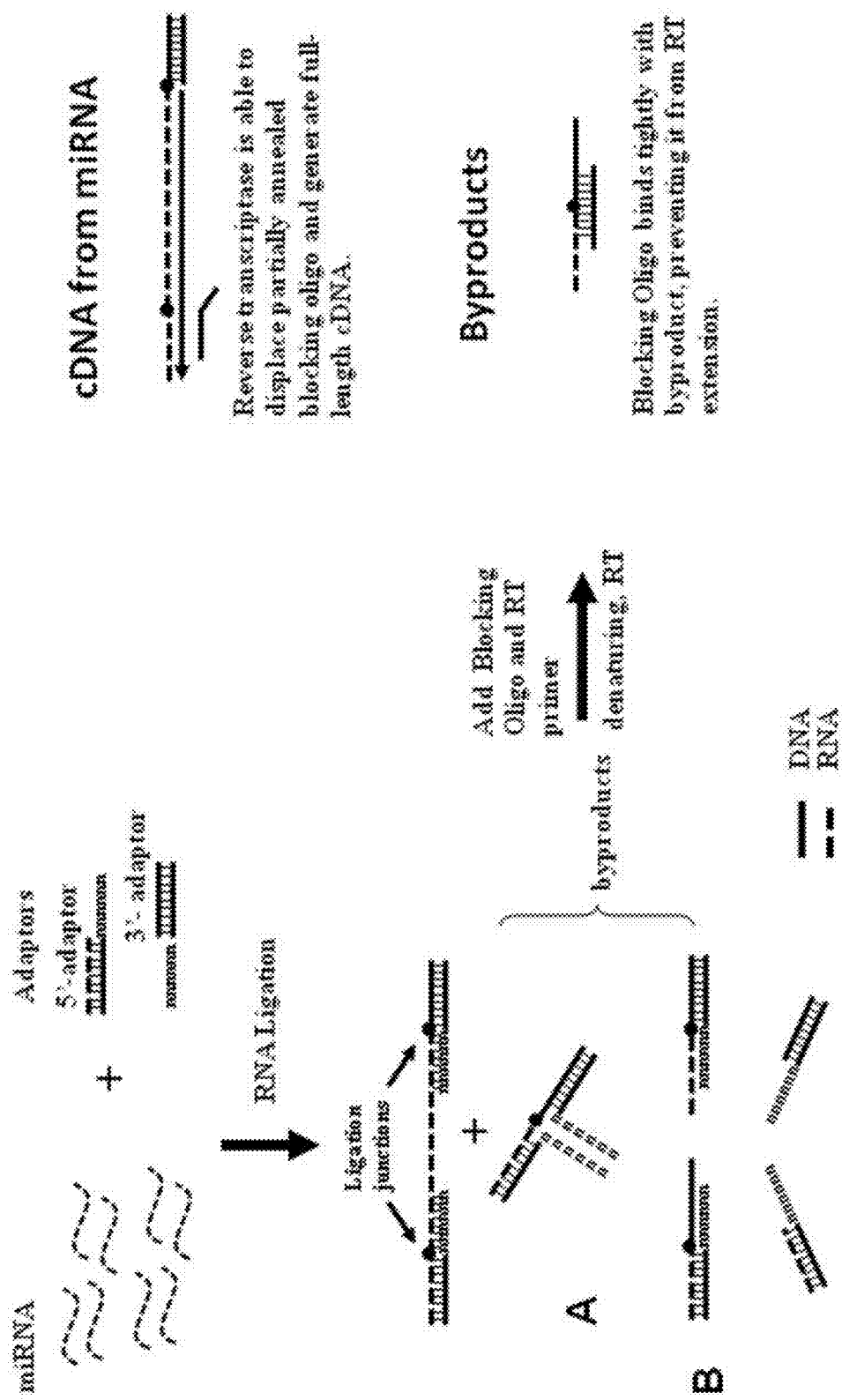
FIG. 1 depicts a process of adding adapter molecules to RNA molecules in preparation to sequencing. A) an adapter:adapter byproduct. B) byproducts where only one of two adapters have been ligated.

FIG. 1 portrays how a blocking oligonucleotide may be used to prevent amplification of byproduct molecules formed during the ligation of adaptor molecules to target nucleic acid molecules. In this non-limiting example, the 5' and 3' adaptor molecules are double stranded molecules with the 5' adaptor having a free 3' tail and the 3' adaptor having a free 5' tail. Further, the 5' adaptor is a hybrid RNA/DNA molecule. However, the function of a blocking oligonucleotide does not depend on either the 5' or 3' adapter comprising an RNA strand. A blocking oligonucleotide would also function in situations where single stranded adapters were used.

Following a ligation reaction, in addition to the desired end-product of a single stranded RNA segment with double stranded adapters covalently linked at each end, undesired byproducts may be formed. These byproducts may include molecules formed by direct ligation of the 5' and 3' adapters to each other without an intervening RNA segment and RNA segments where only one of the 5' or 3' adapters has been ligated. In subsequent amplification reactions, molecules ligated with a single adapter will not be amplified beyond the first round of amplification because they lack the proper complementary sequences at either the 5' or 3' end to hybridize with the polymerase priming sequences. However, byproduct molecules formed by the direct ligation of the 5' and 3' adapters to each other will continue to be amplified because the sequences complimentary to the amplification primers are present at both ends of the molecule. This results in diversion of amplification reaction reagents such as primers and dNTPs from amplification of the desired RNA segment and limits the ultimate yield of properly adapted RNA segments. In order to avoid amplification of undesired byproducts it has been necessary to use gel purification or other purification methods to remove byproducts from the completed ligation reaction prior to further amplification. This additional step in the process lengthens the sample preparation time and reduces the possibility of automating the overall library preparation process.

Provided here is an alternative solution where byproducts are not removed but are inhibited so that they may not be suitable substrates in subsequent amplification reactions. An adapter:adapter product may be inhibited from amplification by constructing an oligonucleotide which tightly binds to the 3' end of the 5' adapter and the 5' end of the 3' adapter such that the oligonucleotide may tightly bind to the junction of the ligated 5' and 3' adapters. With the oligonucleotide bound to the junction of the adapter:adapter byproduct, extension of the molecule by reverse transcriptase is effectively blocked.

Figure 2:
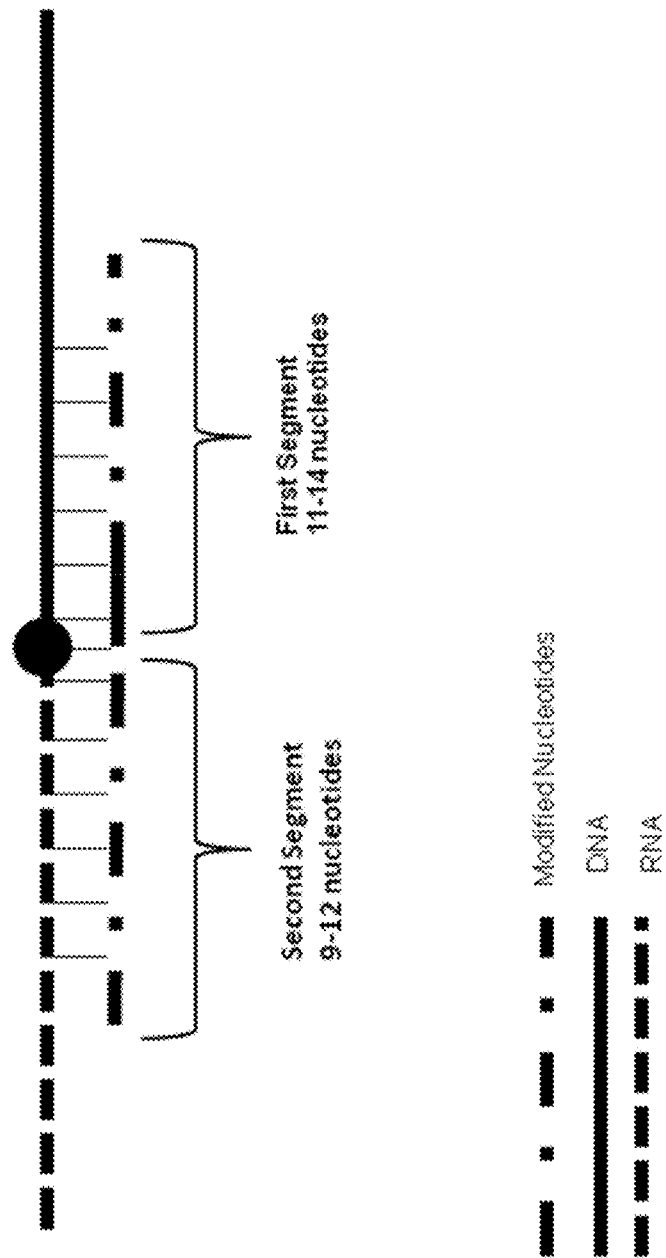
FIG. 2 depicts design considerations of an exemplary blocking oligonucleotide.

Design of an exemplary blocking oligonucleotide is shown in FIG. 2. The overall length of a blocking oligonucleotide may be from 20 to 26 nucleotides in length and comprise at least two segments. Particular embodiments of a blocking oligonucleotide may be 20, 21, 22, 23, 24, 25 or 26 nucleotides in length. A first segment may be at the 5' end of the blocking oligonucleotide and comprise 11-14 nucleotides which are complementary to a 5' end of a 3' adapter. Particular embodiments of a first segment may be 11, 12, 13, or 14 nucleotides in length. A second segment may be at the 3' end of the blocking oligonucleotide and comprise 9-12 nucleotides which may be complementary to the 3' end of a 5' adapter molecule. In some embodiments a second segment may be 9, 10, 11 or 12 nucleotides in length. In further embodiments the 3' end of the second segment is blocked by an amine group, C3 or C6 amino or thiol groups or other groups to prevent extension of the molecule. The 3' terminus could also contain an H and the 2' group is blocked.

In order for the blocking oligonucleotide to function effectively it is desirable that it bind with high affinity to the adapter:adapter byproduct to avoid off-target effects. This can be accomplished by substituting one or more of the nucleotides of the blocking oligonucleotide with modified nucleotides which hybridize with higher affinity. In some embodiments 1, 2, 3, 4, 5, 6, 7, 8, 9, 10, 11 or 12 nucleotides of a first segment are modified nucleotides. In other embodiments 1, 2, 3, 4, 5, 6, 7, 8, 9, 10, 11, 12, 13 or 14 nucleotides of a second segment are modified oligonucleotides.

Suitable modified nucleotides include 2'-O-methyl modified nucleotides, 2'-deoxy-2'-fluoro modified nucleotide, a 2'-deoxy-modified nucleotide, 2'-alkyl-modified nucleotides, locked nucleotides (LNA), nucleotides comprising a 5'-phosphorothioate group, a basic nucleotides, 2'-amino-modified nucleotides, morpholino nucleotides, phosphoramidates, and non-natural base comprising nucleotides.

To ensure that the binding between blocking oligonucleotide and adaptor:adaptor byproduct is highly specific with minimal off-target effects, it may be desirable to lessen the strength of binding (lower the $t_m$) between the blocking oligonucleotide and the adapter:adapter byproduct in a particular region hybridization between the two molecules. For example, it may be advantageous that the 3' end of the first segment hybridize with a lower $t_m$ to the 5' end of the 3' adapter than the hybridization $t_m$ that occurs throughout the rest of the hybridized molecule. In other embodiments the region with a lower $t_m$ may be at the 5' end of the first segment, the 5' end of the second segment or the 3' end of the second segment. The region with a lower $t_m$ may be from 1 to 7 nucleotides in length. In certain embodiments the hybridization region with a lower $t_m$ may be 1, 2, 3, 4, 5, 6 or 7 nucleotides in length. In some embodiments, the $t_m$ is lowered by at least 1° C., at least 5° C. or at least 10° C. In other embodiments the $t_m$ is lowered by 1°-10° C., by from 1°-5° C. or from 5-10° C.

The $t_m$ of hybridization may be lowered by including one or more normal nucleotides which do not hybridize with increased affinity compared to modified nucleotides or by including one or more indiscriminate bases in the sequence of the blocking oligonucleotide. Normal nucleotides and indiscriminant bases may be used alone or together as needed to achieve the desired reduction in $t_m$. The number and location of normal and indiscriminant nucleotides within the blocking oligonucleotide will depend on the particular sequence of the adapter molecules to which the blocking oligonucleotide is intended to hybridize.

An example of an indiscriminate base is isosine. Inosine is a nucleoside that is formed when hypoxanthine is attached to a ribose ring (also known as a ribofuranose) via a β-N9-glycosidic bond. Inosine is commonly found in tRNA and is essential for proper translation of the genetic code in wobble base pairs. Inosine is able to base pair with uridine, adenosine or cytosine and so is considered an indiscriminate base (Gregoire et al., 1989 J. Clin Micro. 27; 2660-2665).

RNA for library preparation may be from total RNA (whole transcriptome) preparations or from particular subsets of RNA such as mRNA or small RNA. For some applications where a blocking oligonucleotide may be used, the nucleic acid to be used for library construction may be a small RNA molecule, that is an RNA less than about 40 nucleotides in length. RNA samples isolated from some sources may contain sufficient small RNA for use with the procedures described herein but in many cases the RNA sample may need to be enriched for small RNA molecules. RNA samples having less than about 0.5% small RNA may need to be enriched for small RNA. Methods for isolating small RNA molecules are well known in the art and a number of kits for this purpose are commercially available including mirVana™ miRNA isolation kit (Life Technologies), Purelink™ miRNA isolation kit (Life Technologies), mirPremier™ miRNA isolation kit (Sigma-Aldrich) and miRNeasy™ kit (Qiagen).

Sequencing adapters to be ligated to the ends of the RNA molecule to be sequenced will vary depending on the specific sequencing platform to be used. Examples of commercial sequencing kits which provide adapters for RNA sequencing include Ion Total RNA-Seq kit (Life Technologies), SOLiD™ Total RNA-Seq kit (Life Technologies) and TruSeq™ RNA Sample Prep kit (Illumina). Adapters may further comprise additional sequences, such as barcodes, which may be useful for multiplexing, sequencing or other uses. To maximize the binding of reverse transcriptase to the upper strand of the 3' adapter, the 3' adapter may have a 3' overhang. Further, in some cases, 3' adapters may contain di-deoxy nucleotides at their 3' termini to minimize self-ligation. The adapters may be ligated or otherwise covalently attached to the ends of the RNA molecule to be sequenced following the manufacturers protocols and use of the manufacturer provided reverse transcription primer to produce cDNA of the adapted RNA molecule. The cDNA may be purified using methods well known in the art.

After purification, the cDNA of the adapted RNA molecule may be amplified by PCR using primers specifically designed for the particular sequencing adapters being used. High fidelity polymerases such as the polymerase included in PLATINUM® PCR SuperMix High Fidelity (Life Technologies) may be used for amplification. The amplified cDNA may be purified using methods well known in the art.

EXAMPLES

Example 1: Synthesis of Blocking Oligonucleotides

Oligonucleotide blockers were chemically synthesized using standard phosphoramidite-based DNA or 2'-O-Me substituted nucleoside monomers with established solid phase oligomerization cycles according to Beaucage, S. L. and Iyer, R. P. (*Tetrahedron*, 1993 (49) 6123; *Tetrahedron*, 1992 (48) 2223). Oligonucleotides were synthesized using DMT-O-C6-phthalamido CPG support. Synthesis of oligonucleotides was performed on a BioAutomation MerMade 192 or BioAutomation MerMade 12 synthesizers (BioAutomation Corp, Plano, Tex.). Eight equivalents of activator were used for every equivalent of phosphoramidite to provide a satisfactory stepwise coupling yield of >98% per base addition. Purification of the oligonucleotide blockers was performed using anion exchange preparative HPLC (Agilent 1200 series) with quaternary ammonium bonded solid phase. The purified oligonucleotides were desalted using a semi-permeable membrane. Analytical HPLC (ion exchange) was used for determining single strand purity, MALDI mass spectrometry was used for determining oligonucleotide identity, and UV spectroscopy was used for quantitative determination of blockers. For DNA and 2'-O-Me purine residues adenine, inosine, and guanine were used. For DNA pyrimidine residues, cytosine and thymidine were used, while for 2'-O-Me pyrimidine residues cytosine and uridine were used.

Procedures for the preparation of 1-(2'-O-methyl-(3-D-ribofuranosyl)-5-nitroindole are described in Gaubert, G.; Wengel, J. *Tetrahedron* Letters 2004, 45, 5629.

Example 2: Exemplary Protocol for Library Preparation Using Blocking Oligonucleotides Use of a blocking oligonucleotide for preparation of a library for sequencing using the Ion Total RNA-Seq Kit is described in the following example. Fragmenting the whole transcriptome RNA involves the following procedures:

1. Fragment the RNA using RNase III
2. Purify the fragmented RNA
3. Assess the yield and size distribution of the fragmented RNA.

Guidelines for RNA Sample Type and Amount

Use 100-500 ng of poly(A) RNA or 200-500 ng of rRNA-depleted total RNA. Use high quality total RNA:

For total RNA, see "Assess the yield and size distribution of the fragmented RNA" below.

For poly(A) RNA, we recommend performing two rounds of oligo(dT) selection of the poly(A) RNA; for example, use the MicroPoly(A)Purist™ Kit. Also, confirm the absence of 18S and 28S rRNA; for example, check the profile of the poly(A) RNA on an Agilent® 2100 Bioanalyzer™ instrument.

For rRNA-depleted total RNA, we recommend that you remove rRNA from total RNA for transcriptome analysis using the RiboMinus™ Eukaryote Kit for RNASeq or the RiboMinus™ Plant Kit for RNA-Seq.

Use the highest quality total RNA possible as your starting material. Ideally, use RNA with an RNA integrity number (RIN) greater than 7. FirstChoice® Total RNA provides high-quality, intact RNA isolated from a variety of sources. Quantitate the amount of RNA in the sample using the NanoDrop Spectrophotometer.

ERCC RNA Spike-in Control Mixes

It is strongly recommend that you add ERCC RNA Spike-In Control Mixes to the input total RNA before RNA depletion or poly(A) selection for whole transcriptome library generation.

The ERCC RNA Spike-In Control Mixes provide a set of external RNA controls that enable performance assessment of a variety of technology platforms used for gene expression experiments. Add one Spike-In Control Mix to each RNA sample, and run these samples on your platform; compare the Spike-In Control Mix data to known Spike-In Control Mix concentrations and ratios to assess the dynamic range, lower limit of detection, and fold-change response of your platform. The following table provides guidelines for how much Spike-In Control Mix to add to the input RNA for whole transcriptome library preparation. For detailed information, refer to the ERCC RNA Spike-In Control Mixes User Guide.

| | Volume of Spike-in Mix 1 or Mix 2 (dilution) | |
|---|---|---|
| Amount of Sample RNA | Total RNA | Poly(A) RNA |
| 20 ng | 4 µl (1:10000) | 2 µl (1:100) |
| 50 ng | 1 µl (1:1000) | 5 µl (1:100) |
| 100 ng | 2 µl (1:1000) | 1 µl (1:10) |
| 500 ng | 1 µl (1:100) | 5 µl (1:10) |
| 1000 ng | 2 µl (1:100) | — |
| 5000 ng | 1 µl (1:10) | — |

† ERCC RNA Spike-In Mix 1, ExFold Spike-In Mix 1, or ExFold Spike-In Mix 2

Fragment the RNA using RNase III
Use components from the Ion Total RNA-Seq Kit v2:
Nuclease-Free Water
10×RNase III Reaction Buffer
RNase III
1. On ice, assemble a reaction for each RNA sample in a 0.2-mL PCR tube:

| Component (add in the order shown) | Volume for one reaction |
|---|---|
| RNA sample and Nuclease-Free Water: | 8 µl |
| Poly(A) RNA: 100-500 ng | |
| rRNA-depleted total RNA: 200-500 ng | |
| WT Control RNA: 500 ng | |
| 10X RNase III Reaction Buffer | 1 µl |
| RNase III | 1 µl |
| Total volume | 10 µl |

2. Flick the tube or pipet up and down a few times to mix, then spin briefly.
3. Incubate the reaction in a thermal cycler at 37° C. for 10 minutes.
4. Immediately after the incubation, add 20 µL of Nuclease-Free Water, then place the fragmented RNA on ice.
Purify the Fragmented RNA
Add 44 mL of 100% ethanol to bottle of the Wash Solution Concentrate and mix well. Mark the label on the bottle to indicate that you added ethanol. Store the solution at room temperature.
If you see a white precipitate in the Binding Solution Concentrate, warm the solution at 37° C., then shake the solution to dissolve any precipitate before use.
Incubate the Nuclease-Free Water at 37° C. for >5 minutes.
1. Prepare beads for each sample:
a. Gently vortex the Nucleic Acid Binding Beads tube to completely resuspend the magnetic beads.
b. Add 5 µL beads to wells on the Processing Plate.
c. Add 90 µL Binding Solution Concentrate to each well, then mix the Concentrate and beads by pipetting up and down 10 times.
2. Bind the fragment RNA products to the beads:
a. Transfer each 30-µL fragment RNA reaction to a well with beads of the Processing Plate.
b. Set a P200 pipette at 150 µL. Attach a new 200-µL tip to the pipette, then prewet the new 200-µL tip with 100% ethanol by pipetting the ethanol up and down 3 times.
c. Without changing tips, add 150 µL of 100% ethanol to each well.
d. Mix and incubate the samples off of the magnetic stand. Mix the suspension in each well thoroughly by pipetting the wells up and down 10 times, then incubate the samples for 5 minutes at room temperature (15° C. to 30° C.).
Note: The color of the mixture should be homogeneous after mixing.
3. Remove the supernatant from the beads:
a. Place the Processing Plate on a magnetic stand for 5-6 minutes to separate the beads from the solution. Wait for the solution to clear before proceeding to the next step.
b. Leaving the Processing Plate on the magnetic stand, aspirate and discard the supernatant from the plate.
4. Wash the beads with Wash Solution Concentrate with ethanol:
a. Leave the Processing Plate on the magnetic stand.
b. Add 150 µL of Wash Solution Concentrate with ethanol to each sample.
c. Incubate the samples at room temperature (15° C. to 30° C.) for 30 seconds.
5. Remove the supernatant from the beads:
a. Aspirate and discard the supernatant from the plate.
b. Use a P10 or P20 pipette to remove residual ethanol.
c. Air-dry the beads at room temperature (15° C. to 30° C.) to remove all traces of ethanol by leaving the Processing Plate on the magnetic stand for 1-2 minutes.
6. Elute the fragmented RNA from the beads:
a. Remove the Processing Plate from the magnetic stand.
b. Add 12 µL of pre-warmed (37° C.) Nuclease-Free Water to each sample, then mix the Nuclease-Free Water and beads by pipetting up and down 10 times.
c. Incubate at room temperature (15° C. to 30° C.) for 1 minute.
d. Place the Processing Plate on the magnetic stand for 1 minute to separate the beads from the solution. Wait for the solution to clear before proceeding to the next step.
e. For each sample, collect the eluent.
Assess the Yield and Size Distribution of the Fragmented RNA
Use the Qubit® RNA Assay Kit with the Qubit® Fluorometer and the Agilent® RNA 6000 Pico Kit with the Agilent® 2100 Bioanalyzer™ instrument.
Note: You can use a NanoDrop® Spectrophotometer in place of the Qubit RNA Assay Kit and Qubit Fluorometer. For increased accuracy, we recommend that you quantitate the RNA concentration using the Qubit RNA Assay Kit with the Qubit Fluorometer.
1. Quantitate the yield of the fragmented RNA using the Qubit RNA Assay Kit with the Qubit Fluorometer.
Refer to the Qubit® RNA Assay Kit Protocol or the Qubit® Fluorometer Instruction Manual for instructions.
2. Assess the size distribution of the fragmented RNA:
a. Dilute 1 µL of the sample 1:10 with Nuclease-Free Water.
b. Run the diluted sample on an Agilent 2100 Bioanalyzer instrument with the RNA 6000 Pico Kit. Follow the manufacturer's instructions for performing the assay.
c. Using the 2100 expert software, review the size distribution.
The fragmentation procedure should produce a distribution of RNA fragment sizes from 35 nt to several hundred or a few thousand nt, depending on your sample type. The average size should be 100-200 nt.
Note: For instructions on how to review the size distribution, refer to the Agilent® 2100 Bioanalyzer™ Expert User's Guide.

Proceed according to the amount of fragmented RNA you have in 3 µL:

| Amount of fragmented RNA in 3 µL | Instructions |
|---|---|
| ≥50 ng of poly(A) RNA<br>≥100 ng of rRNA-depleted total RNA<br>≥100 ng of WT Control RNA | Proceed to "Construct the whole transcriptome library"<br>Store the remaining RNA at -80° C. |
| <50 ng of poly(A) RNA<br><100 of ng rRNA-depleted total RNA | 1. Dry 50-100 ng of the RNA completely in a centrifugal vacuum concentrator at low or medium heat (≤40° C.); this should take 10-20 minutes.<br>2. Resuspend in 3 µL of Nuclease-Free Water, then proceed to "Construct the whole transcriptome library". |

Construct the Whole Transcriptome Library

Hybridize and Ligate the RNA

1. On ice, prepare the hybridization master mix:

| Component | Volume for one reaction* |
|---|---|
| Ion Adapter Mix V2 | 2 µl |
| Hybridization Solution | 3 µl |
| Total volume | 5 µl |

*Include 5-10% excess volume to compensate for pipetting error when preparing the master mix.

2. Add 5 µL of hybridization master mix to 3 µL of fragmented RNA sample:

Fragmented poly(A) RNA: 50 ng

Fragmented rRNA-depleted total RNA: 100 ng

3. Slowly pipet the solution up and down 10 times to mix, then spin briefly.

4. Run the hybridization reaction in a thermal cycler:

| Temperature | Time |
|---|---|
| 65° C. | 10 min. |
| 30° C. | 5 min. |

5. On ice, add the RNA ligation reagents to the 8-pt hybridization reactions:

a. Combine:

| Component | Volume for one reaction* |
|---|---|
| Hybridization reaction | 8 µl |
| 2X Ligation Buffer | 10 µl |
| Ligation Enzyme Mix | 2 µl |
| Total volume | 20 µl |

*Include 5-10% excess volume to compensate for pipetting error when preparing the master mix.

b. Flick the tube or slowly pipet the solution up and down a few times to mix well, then spin briefly.

6. Incubate the 20-pt ligation reactions in a thermal cycler at 30° C. for 30 minutes.

Perform Reverse Transcription (RT)

0.1. On ice, prepare the RT master mix:

| Component | Volume for one reaction* |
|---|---|
| Nuclease free water | 2 µl |
| 10X RT Buffer | 4 µl |
| 2.5 mM dNTP Mix | 2 µl |
| Ion RT Primer v2 | 8 µl |
| Total volume | 16 µl |

*Include 5-10% excess volume to compensate for pipetting error when preparing the master mix.

2. Incubate the RT master mix with the ligated RNA sample:

a. Add 16 µL of the RT master mix to each 20-µL ligation reaction.

b. Gently vortex the reaction to mix thoroughly, then spin the reaction briefly.

c. Incubate in a thermal cycler with a heated lid at 70° C. for 10 minutes, then snap-cool on ice.

3. Perform the reverse transcription reaction:

a. Add 4 µL of 10× SuperScript® III Enzyme Mix to each ligated RNA sample.

b. Gently vortex to mix thoroughly, then spin briefly.

c. Incubate in a thermal cycler with a heated lid at 42° C. for 30 minutes.

Purify the cDNA

1. Prepare beads for each sample:

a. Gently vortex the Nucleic Acid Binding Beads tube to completely resuspend the magnetic beads.

b. Add 10 µL beads to wells on the Processing Plate.

c. Add 120 µL Binding Solution Concentrate to each well, then mix the Binding Solution Concentrate and beads by pipetting up and down 10 times.

2. Bind the cDNA to the beads:

a. Add 60 µL of Nuclease-Free Water to each of the 40-µL RT reaction.

b. Transfer each 100-µL RT reaction to a well with beads of the Processing Plate.

c. Set a P200 pipette at 125 pt. Attach a new 200-µL tip to the pipette, then prewet the new 200-µL tip with 100% ethanol by pipetting the ethanol up and down 3 times.

d. Without changing tips, add 125 µL of 100% ethanol to each well.

e. Mix and incubate the samples off of the magnetic stand. Mix the suspension in each well thoroughly by pipetting the wells up and down 10 times, then incubate the samples for 5 minutes at 15° C. to 30° C.

Note: The color of the mixture should be homogeneous after mixing.

3. Remove the supernatant from the beads:

a. Place the Processing Plate on a magnetic stand for 5-6 minutes to separate the beads from the solution. Wait for the solution to clear before proceeding to the next step.

b. Leaving the Processing Plate on the magnetic stand, aspirate and discard the supernatant from the plate.

4. Wash the beads with Wash Solution Concentrate with ethanol:

a. Leave the Processing Plate on the magnetic stand.

b. Add 150 µL of Wash Solution Concentrate with ethanol to each sample.

c. Incubate the samples at room temperature (15° C. to 30° C.) for 30 seconds.

5. Remove the supernatant from the beads:

a. Aspirate and discard the supernatant from the plate.

b. Use a P10 or P20 pipette to remove residual ethanol.

c. Air-dry the beads at room temperature (15° C. to 30° C.) to remove all traces of ethanol by leaving the Processing Plate on the magnetic stand for 1-2 minutes.

6. Elute the cDNA from the beads:

a. Remove the Processing Plate from the magnetic stand.

b. Add 12 µL of pre-warmed (37° C.) Nuclease-Free Water to each sample, then mix the Nuclease-Free Water and beads by pipetting up and down 10 times.

c. Incubate at room temperature (15° C. to 30° C.) for 1 minute.

d. Place the Processing Plate on the magnetic stand for 1 minute to separate the beads from the solution. Wait for the solution to clear before proceeding to the next step.

e. For each sample, collect the eluent.

Amplify the cDNA

1. For each cDNA sample, prepare 47 µL of PCR Master Mix:

| Component | Volume for one reaction* |
| --- | --- |
| Platinum PCR SuperMix High Fidelity** | 45.0 µl |
| Ion 5' PCR Primer v2 | 1.0 µl |
| Ion 3' PCR Primer v2 | 1.0 µl |
| Total volume | 47.0 µl |

*Include 5-10% excess volume to compensate for pipetting error when preparing the master mix.
**Platinum® PCR SuperMix High Fidelity contains a proofreading enzyme for high fidelity amplification.

2. Transfer 6 µL of cDNA to a new PCR tube.

3. Add 47 µL of the PCR master mix to each 6 µL of cDNA.

4. Flick the tube or slowly pipet the solution up and down a few times to mix well, then spin briefly.

5. Run the PCRs in a thermal cycler:

| Stage | Temp | Time |
| --- | --- | --- |
| Hold | 94° C. | 2 min. |
| Cycle (2 cycles) | 94° C. | 30 sec. |
|  | 50° C. | 30 sec. |
|  | 68° C. | 30 sec. |
| Cycle (14 cycles) | 94° C. | 30 sec. |
|  | 62° C. | 30 sec. |
|  | 68° C. | 30 sec. |
| Hold | 68° C. | 5 min. |

Purify the Amplified cDNA

Prepare beads for each sample:

a. Gently vortex the Nucleic Acid Binding Beads tube to completely resuspend the magnetic beads.

b. Add 10 µL beads to wells on the Processing Plate.

c. Add 180 µL Binding Solution Concentrate to each well, then mix the Concentrate and beads by pipetting up and down 10 times.

2. Bind the amplified cDNA to the beads:

a. Transfer each 53-µL of the amplified cDNA to a well with beads of the Processing Plate.

b. Set a P200 pipette at 130 µL. Attach a new 200-µL tip to the pipette, then prewet the new 200-µL tip with 100% ethanol by pipetting the ethanol up and down 3 times.

c. Without changing tips, add 130 µL of 100% ethanol to each well.

d. Mix and incubate the samples off of the magnetic stand. Mix the suspension in each well thoroughly by pipetting the wells up and down 10 times, then incubate the samples for 5 minutes at room temperature (15° C. to 30° C.).

Note: The color of the mixture should be homogeneous after mixing.

3. Remove the supernatant from the beads:

a. Place the Processing Plate on a magnetic stand for 5-6 minutes to separate the beads from the solution. Wait for the solution to clear before proceeding to the next step.

b. Leaving the Processing Plate on the magnetic stand, aspirate and discard the supernatant from the plate.

4. Wash the beads with Wash Solution Concentrate with ethanol:

a. Leave the Processing Plate on the magnetic stand.

b. Add 150 µL of Wash Solution Concentrate with ethanol to each sample.

c. Incubate the samples at room temperature (15° C. to 30° C.) for 30 seconds.

5. Remove the supernatant from the beads:

a. Aspirate and discard the supernatant from the plate.

b. Use a P10 or P20 pipette to remove residual ethanol.

c. Air-dry the beads at room temperature (15° C. to 30° C.) to remove all traces of ethanol by leaving the Processing Plate on the magnetic stand for 1-2 minutes.

6. Elute the cDNA from the beads:

a. Remove the Processing Plate from the magnetic stand.

b. Add 15 µL of pre-warmed (37° C.) Nuclease-Free Water to each sample, then mix the Nuclease-Free Water and beads by pipetting up and down 10 times.

c. Incubate at room temperature (15° C. to 30° C.) for 1 minute.

d. Place the Processing Plate on the magnetic stand for 1 minute to separate the beads from the solution. Wait for the solution to clear before proceeding to the next step.

e. For each sample, collect the eluent.

Assess the Yield and Size Distribution of the Amplified DNA.

Use a NanoDrop® Spectrophotometer, and the Agilent® 2100 Bioanalyzer™ instrument with the Agilent® DNA 1000 Kit.

1. Measure the concentration of the purified DNA with a NanoDrop Spectrophotometer; if needed, dilute the DNA to <50 ng/µL for accurate quantitation with the DNA 1000 Kit.

2. Run 1 µL of the purified DNA on an Agilent 2100 Bioanalyzer instrument with the DNA 1000 Kit. Follow the manufacturer's instructions for performing the assay.

3. Using the 2100 expert software, perform a smear analysis to quantify the percentage of DNA that is 25-160 bp.

4. Determine the median peak size (bp) and molar concentration (nM) of the cDNA library using the Agilent software.

Note: The mass concentration of the cDNA must be <50 ng/pt for accurate quantitation with the DNA 1000 Kit.

Alternatively, obtain the mass concentration by another method, and convert the mass concentration to molar concentration.

Example 3: Exemplary Protocol for Small RNA Library Preparation Using Blocking Oligonucleotides Use of a blocking oligonucleotide for preparation of a library for sequencing using the Ion Total RNA-Seq Kit is described in the following example. For use in this procedure, RNA should contain a small RNA fraction (<40 nt). Optimal results may be obtained when RNA that has been size selected for small RNA is used. RNA samples vary widely in small RNA content, based on their source and the RNA isolation method. The proportion of small RNA is high enough in some tissues to allow efficient library preparation from total RNA. Many tissues and most cell lines, however, contain a small fraction of small RNA. For these samples enrichment for small RNA is recommended. An Agilent small RNA chip may be used to determine the concentration of miRNA (10-40 nts) in the total RNA or enriched small RNA sample.

The quality of the total RNA sample may be determined using the NanoDrop® Spectrophotometer and the Agilent® 2100 Bioanalyzer™ instrument with the Agilent® RNA 6000 Nano Kit and the Agilent® Small RNA Kit.

1. Quantitate the amount of RNA in the sample using the NanoDrop Spectrophotometer.

2. Determine the quality of the small RNA in your sample:
a. Dilute the RNA to ~50 to 100 ng/μL.
b. Run 1 μL of diluted RNA on the Agilent RNA 6000 Nano chip to determine the concentration of total RNA. Follow the manufacturer's instructions for performing the assay.
c. Using the 2100 expert software, determine the mass of total RNA in the sample, and save for step 3c (calculating the miRNA content).
d. Using the 2100 expert software, review the RNA Integrity Number (RIN). The highest quality library mapping statistics are obtained from input RNA with higher RIN values.

3. Determine the percentage of small RNA in your sample:
a. Run 1 μL of diluted RNA on Agilent Small RNA chip. Follow the manufacturer's instructions for performing the assay.
b. Using the 2100 expert software, determine the mass of small RNA (miRNA) (10-40 nt) from the Small RNA Kit chip.
c. Calculate the miRNA content in your RNA sample using the formula:

$$\% \text{ miRNA} = (\text{mass of miRNA} \div \text{mass of total RNA}) \times 100$$

4. Determine whether small RNA enrichment is needed and the type of enrichment to perform:

| How much miRNA (10-40 nt) is in your RNA sample? | Recommendations for small RNA enrichment and next steps |
|---|---|
| ≥0.5% miRNA | You can use the total RNA in the ligation reaction, and small RNA enrichment is not needed. However, for optimal results, enrichment of all total RNA samples is recommended. |
| <0.5% miRNA | Small RNA enrichment is strongly recommended. The Invitrogen PureLink® miRNA Isolation Kit may be used. |

Small RNA Enrichment

This purification procedure is designed for enriching small RNA from total RNA sample.

1. Resuspend 1-50 μg total RNA in 90 μL of nuclease-free water. Add 300 μL Binding Buffer (L3) and 210 μL 100% Ethanol. Mix well by vortexing.

2. Load 600 μL sample to the Spin Cartridge and centrifuge at 12,000×g for 1 minute. Total RNA is bound to the cartridge and small RNA is in the flow through.

3. Keep the flow through. Transfer the flow through to a clean 1.5-mL tube. Add 700 μL 100% ethanol to the flow through and mix well by vortexing.

4. Transfer 700 μL sample from step 3 to a second Spin Cartridge. Spin at 12,000×g for 1 minute at room temperature. Small RNA molecules bind to the Spin cartridge. Discard the flow through.

5. Repeat step 4 for the remaining sample. Place the Spin cartridge in the collection tube.

6. Wash the Spin Cartridge with 500 μL Wash Buffer (W5) with ethanol. Centrifuge at 12,000×g for 1 minute. Discard the flow-through and repeat once.

7. Discard the collection tube and place the Spin Cartridge in a Wash Tube supplied with the kit. Centrifuge the Spin Cartridge at 16,000×g for 3 minutes to remove any residual Wash Buffer.

8. Place the Spin Cartridge to a clean Recovery Tube. Add 50 μL of RNase-free water to the center of the Spin Cartridge.

9. Incubate at room temperature for 1 minute.

10. Centrifuge at 16,000×g for 1 minute to recover enriched small RNA from the cartridge.

11. Store small RNA at −80° C. or check small RNA quality on Agilent Small RNA chip. Speed vac to concentrate samples if necessary.

Assess the Quality and Quantity of Samples that are Enriched for Small RNA

Assess the quality and quantity of samples that are enriched for small RNA using the Agilent® 2100 Bioanalyzer™ instrument with the Agilent® Small RNA Kit.

1. Run 1 μL of purified and enriched small RNA sample on the Agilent 2100 Bioanalyzer instrument with the Small RNA Kit chip. Follow the manufacturer's instructions for performing the assay.

2. Compare the bioanalyzer traces to those of the sample before enrichment (step 2 in "Assess the amount and quality of small RNA in your total RNA samples"), and determine whether the RNA is degraded. For enriched small RNA samples, peaks should be from 10-200 nt.

Determine the Input Amount

Using the results from the Agilent 2100 Bioanalyzer instrument and the Small RNA Kit, determine the amount of total RNA to use according to the type of RNA you ran and the amount of miRNA in 1 μL:

| Input sample type | miRNA (10-40 nts) input range (small RNA chip quantitation) | Total RNA mass |
|---|---|---|
| Total RNA | 5-25 ng | ≤1 μg |
| Enriched small RNA | 1-25 ng | ≤1 μg |

Construct the Small RNA Library

Constructing the small RNA library may comprise the following:

1. Hybridize and ligate the small RNA
2. Perform reverse transcription
3. Purify cDNA using MAGMAX™ beads
4. Amplify the cDNA Purify the amplified DNA using MAGMAX™ beads
6. Assess the yield and size distribution of the amplified DNA Hybridize and Ligate the Small RNA The following components may be used from the Ion Total RNA-Seq Kit:

Hybridization Solution

Nuclease-free Water

2× Ligation Buffer

Ligation Enzyme Mix
1. On ice, prepare the hybridization master mix:

| Component | Volume for one reaction |
| --- | --- |
| Hybridization Solution | 3 μL |
| IA10 Adaptor Mix | 2 μL |
| Total volume per reaction | 5 μL |

2. Transfer 5 μL hybridization master mix to 3 μL enriched small RNA/total RNA sample.
3. Slowly pipet up and down a few times to mix well, then spin briefly.
4. Run the hybridization reaction in a thermal cycler:

| Temperature | Time |
| --- | --- |
| 65° C. | 10 min |
| 16° C. | 5 min |

5. Add the RNA ligation reagents to the 8-μL hybridization reactions:

| Component (add in order shown) | Volume (μL) |
| --- | --- |
| 2X Ligation Buffer | 10 μL |
| Ligation Enzyme Mix | 2 μL |

6. Flick the tube or slowly pipet up and down a few times to mix well, then spin briefly.
7. Incubate the 20-μL ligation reaction in a thermal cycler at 16° C. for 2 hours.

Perform Reverse Transcription

The following components may be used from the Ion Total RNA-Seq Kit:
Nuclease-free Water
dNTP Mix
Ion RT Primer The following components may be used from the VILO cDNA synthesis kit:
10× SuperScript III Enzyme Mix 1. Prepare RT master mix (without the 10× SuperScript III Enzyme Mix):

| Component | Volume for one reaction |
| --- | --- |
| Nuclease-free water | 3 μL |
| 10X RT Buffer | 4 μL |
| dNTP Mix | 2 μL |
| Ion RT Primer | 2 μL |
| Blocking Oligo, 200 μM | 5 μL |
| Total volume per reaction | 16 μL |

2. Incubate the RT master mix with the ligated RNA sample:
a. Add 16 μL of RT master mix to each 20 μL ligation reaction.
b. Pipet up and down a few times to mix, then spin briefly.
c. Incubate in a thermal cycler with a heated lid at 70° C. for 10 minutes, then snap-cool on ice.
3. Perform the reverse transcription reaction:
a. Add 4 μL 10× SuperScript Enzyme Mix to each ligated RNA sample.
b. Gently vortex to mix thoroughly, then spin briefly.
c. Incubate in a thermal cycler with a heated lid at 42° C. for 30 minutes.

Purify cDNA Using MAGMAX™ Beads

The following components may be used from the MAGMAX™-96 total RNA isolation kit:
Lysis/Binding Solution Concentrate
Wash Solution 2 Concentrate Before using the kit, complete Wash Solution 2 by adding 44 mL 100% ethanol to the bottle labeled Wash Solution 2 Concentrate and mix well. Mark the labels of the solutions to indicate that ethanol was added. Store the solution at room temperature. Nuclease-free water should be incubated at 37° C. for at least 5 minutes before start.

1. Prepare beads for each sample
a. Gently vortex the RNA Binding Beads bottle to resuspend the magnetic beads.
b. Add 7 μL beads to wells on a 96-well plate.
c. Add 140 μL MAGMAX™™ Lysis/Binding Solution Concentrate to each well, mix by pipetting up and down 10 times or shaking for 30 s at speed 8.
2. Bind undesired cDNA products to the beads
a. Transfer 40 μL RT reaction to the beads on 96-well plate.
b. Add 120 μL 100% Ethanol to each well.
c. Mix thoroughly by pipette mixing 10 times or shaking for 1 minute at speed 7 on plate shaker. (Note: The color of the mixture should appear homogenous after mixing)
d. Incubate samples for 5 minutes at room temperature off the magnetic stand.
e. Once complete, let samples collect on magnetic stand for 3 minutes or until the supernatant is clear.
f. Carefully aspirate and transfer the supernatant to fresh wells without disturbing the beads. Remove the plate from the magnetic stand.
3. Bind desired cDNA products to the beads
a. Add 78 μL 100% Ethanol and 72 μL nuclease-free water to each well.
b. Mix magnetic beads and add 7 μL to each well
c. Mix thoroughly by pipette mixing 10 times or shaking for 1 minute at speed 7 on plate shaker. (Note: The color of the mixture should appear homogenous after mixing)
d. Incubate samples for 5 minutes at room temperature off the magnetic stand.
e. Once complete, let samples collect on magnetic stand for 4 minutes or until the supernatant is clear.
f. Carefully aspirate and discard the supernatant. Leave the plate on the magnetic stand.
4. Wash the beads with Wash Buffer 2 (W2)
a. Add 150 μL Wash Buffer 2 to each well while on the magnetic stand.
b. Incubate samples for 30 seconds.
c. Aspirate and discard the supernatant.
d. Air dry the beads at room temperature for 3 minutes to remove all traces of ethanol. (Note: Do not overdry the beads. Overdried beads appear cracked.)
e. Remove the plate from the magnetic stand.
5. Elute the cDNA
a. Add 12 μL pre-warmed nuclease-free water (at 37° C.) to each well.
b. Resuspend the beads thoroughly by pipette mixing 10 times.
c. Incubate for 1 minute at room temperature.
d. Place 1.2 mL 96-well plate back on magnetic stand for 1 minute to separate the beads from solution.
e. Collect the 12 μL eluent.

Amplify the cDNA

The following components may be used from the Ion Total RNA-Seq Kit:

Ion 3' PCR Primer

The following components may be used from the Platinum® PCR SuperMix High Fidelity:

HiFi Platinum PCR SuperMix

1. For each cDNA sample, prepare 47 µL PCR master mix:

| Component | Volume (µL) |
| --- | --- |
| HiFi Platinum PCR SuperMix | 45 µL |
| Ion 3' PCR Primer v2 | 1 µL |
| Ion 5' PCR Primer v2 | 1 µL |
| Total volume | 47 µL |

2. Transfer 3 µL of cDNA to a new PCR tube.
3. Transfer 47 µL PCR master mix into each 3 µL cDNA sample.
4. Run the PCR reactions in a thermal cycler:

| Stage | Temp | Time |
| --- | --- | --- |
| Hold | 94° C. | 2 min |
| Cycle (2 Cycles) | 94° C. | 30 sec |
|  | 50° C. | 30 sec |
|  | 68° C. | 30 sec |
| Cycle (14 Cycles) | 94° C. | 30 sec |
|  | 62° C. | 30 sec |
|  | 68° C. | 30 sec |
| Hold | 68° C. | 5 min |

Purify the Amplified DNA

The following components may be used from the MAGMAX™-96 total RNA isolation kit:
Lysis/Binding Solution Concentrate
Wash Solution 2 Concentrate (prepared with ethanol for cDNA cleanup)

1. Prepare beads
a. Gently vortex the RNA Binding Beads bottle to resuspend the magnetic beads.
b. Add 7 µL beads to wells on a 96-well plate that you plan to use.
c. Add 140 µL MAGMAX™ Lysis/Binding Solution Concentrate to the beads and mix by pipetting up and down 10 times or shaking for 30 s at speed 8.

2. Bind amplified cDNA to the beads.
a. Transfer 50 µL PCR reaction to the beads on 96-well plate.
b. Add 110 µL 100% Ethanol to each well.
c. Mix thoroughly by pipette mixing 10 times or shaking for 1 minute at speed 7 on plate shaker. (Note: The color of the mixture should appear homogenous after mixing)
d. Incubate samples for 5 minutes at room temperature off the magnetic stand.
e. Once complete, let samples collect on magnetic stand for 5 minutes or until the supernatant is clear.
f. Carefully aspirate and transfer the supernatant to fresh wells without disturbing the beads. Remove the plate from the magnetic stand.

3. Bind correct cDNA products to the beads
a. Add 35 µL 100% Ethanol and 35 ul of nuclease-free water to each well.
b. Mix magnetic beads and add 7 µL to each well c. Mix thoroughly by pipette mixing 10 times or shaking for 1 minute at speed 7 on plate shaker. (Note: The color of the mixture should appear homogenous after mixing)
d. Incubate samples for 5 minutes at room temperature off the magnetic stand.
e. Once complete, let samples collect on magnetic stand for 5 minutes or until the supernatant is clear.
f. Carefully aspirate and discard the supernatant. Leave the plate on the magnetic stand.

4. Wash the beads with Wash Buffer 2 (W2)
a. Add 150 µL Wash Buffer 2 to each well while on magnetic stand.
b. Incubate samples for 30 seconds.
c. Aspirate and discard the supernatant.
d. Air dry the beads at room temperature for 3 minutes to remove all traces of ethanol. (Note: Do not overdry the beads. Overdried beads appear cracked.)
e. Remove the plate from the Magnetic Stand.

5. Elute the cDNA
a. Add 15 µL pre-warmed nuclease-free water (at 37° C.) to each well.
b. Resuspend the beads thoroughly by pipette mixing 10 times.
c. Incubate for 1 minute at room temperature.
d. Place 1.2 mL 96-well plate back on Magnetic Stand-96 for 1 minute to separate the beads from solution.
e. Collect the 15 µL eluent.

Assess the yield and size distribution of the amplified DNA

A 1 µL aliquot of the sample may be analyzed on an Agilent DNA 1000 chip to assess the yield and size distribution.

Example 4: Library Preparation Using a Blocking Oligonucleotide

A blocking oligonucleotide was used for preparation of a sequencing library for use with the Ion Total RNA-Seq Kit. The level of miRNA in the sample was 2.2% as determined using an Agilent small RNA chip.

The sample was found to have an RIN of 8.8 as determined using the NanoDrop® Spectrophotometer and Agilent® 2100 Bioanalyzer™ as described above.

Using the Ion Total RNA-Seq Kit, 3 µL of the RNA sample was hybridized and ligated to the 5 and 3' adapters according to the manufacturer's directions. The sequence of the 5' adapter was:

```
5' CCTGCGTGTCTCCGACTCAG 3'           (SEQ ID NO: 1)

3' GGACGCACAGAGGCTGAGTCNNNNNNN 5'    (SEQ ID NO: 2)
```

The sequence of the 3' adapter was:

```
5' ATCACCGACTGCCCATAGAGAGG 3'        (SEQ ID NO: 3)

3' NNNNNNNTAGTGGCTGA 5'              (SEQ ID NO: 4)
```

As an alternative, the 3' adapter may contain a di-deoxy nucleotide at the 3' end to minimize formation of self ligation products. For example:

```
5' ATCACCGACTGCCCATAGAGAGGddC 3'     (SEQ ID NO: 5)
```

The ligated molecule was then reverse transcribed as described above using the RT primer:

5' CCTCTCTATGGGCAGTCG 3'    (SEQ ID NO: 6)

and the blocking oligonucleotide:

5' GCAGTCGGTGAT CTGAGTCGGAGA 3'    (SEQ ID NO: 7)

wherein nucleotides 1-7, and 13-24 have 2'-O-methyl modifications and the 3' terminal cytosine is further modified with an amine.

Purification of the resulting cDNA was performed using MAGMAX™ beads as described above. The purified cDNA was then amplified as described above using the following primers and thermocycler reaction times:

5' primer
                                    (SEQ ID NO: 14)
    5' CCATCTCATCCCTGCGTGTCTCCGACTCAG 3'

3' primer
                                    (SEQ ID NO: 8)
    5' CCGCTTTCCTCTCTATGGGCAGTCGGTGAT 3'

| Stage | Temp | Time |
| --- | --- | --- |
| Hold | 94° C. | 2 min |
| Cycle (2 Cycles) | 94° C. | 30 sec |
|  | 50° C. | 30 sec |
|  | 68° C. | 30 sec |
| Cycle (14 Cycles) | 94° C. | 30 sec |
|  | 62° C. | 30 sec |
|  | 68° C. | 30 sec |
| Hold | 68° C. | 5 min |

Amplified cDNA was purified using the MAGMAX™-96 total RNA isolation kit according to the manufacturer's instructions.

Assess the Yield and Size Distribution of the Amplified DNA

Figure 3:
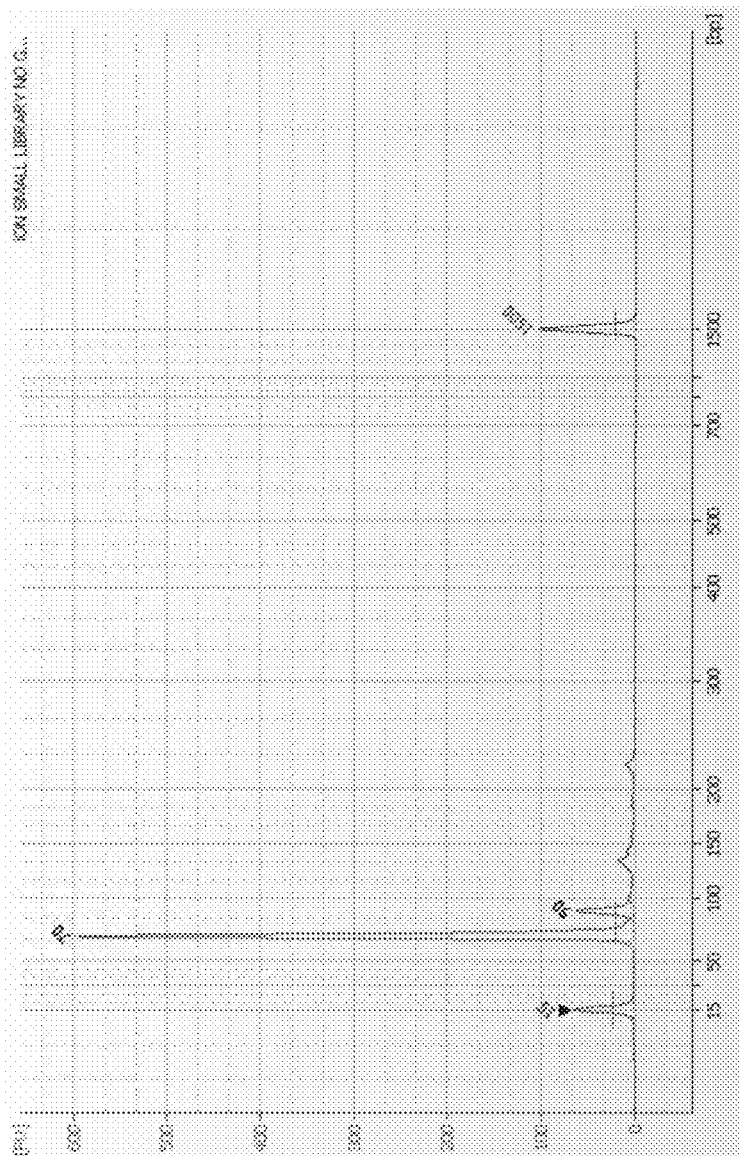
FIG. 3 Bioanalyzer trace for small RNA library with neither gel size selection nor blocking oligo.
Figure 4:
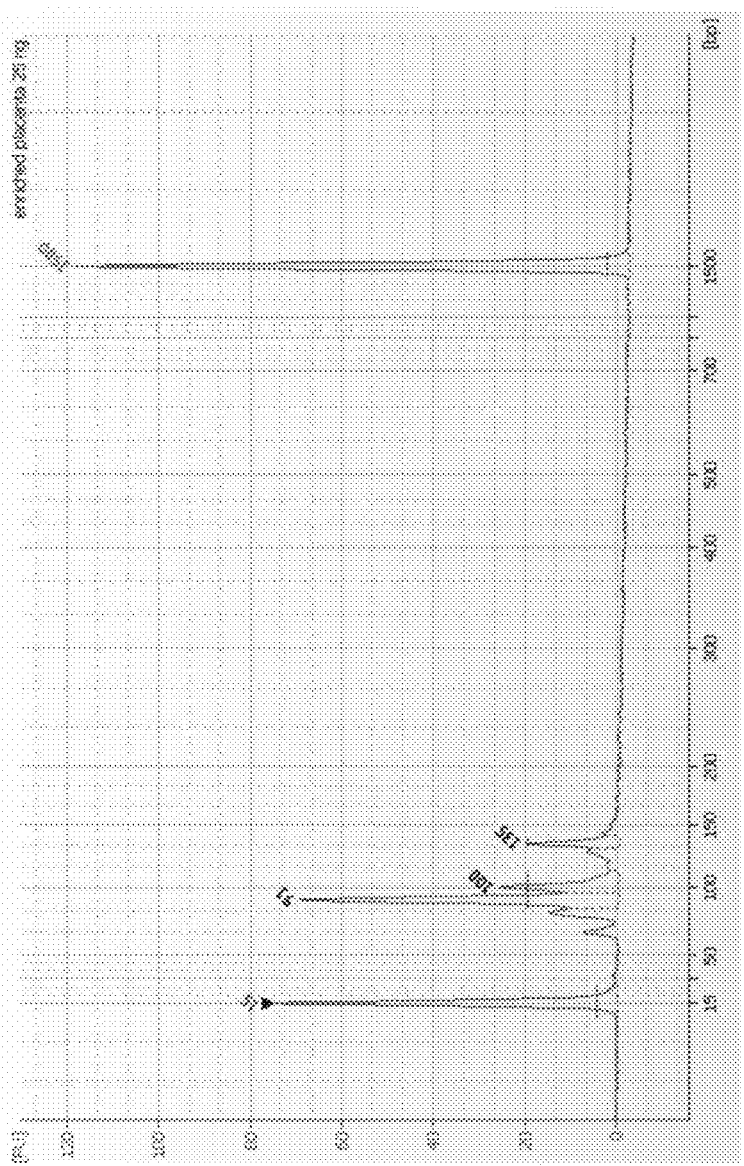
FIG. 4 Bioanalyzer trace for small RNA library using blocking oligo with 2'-O-methyl modifications.

A 1 µL aliquot of the sample may be analyzed on an Agilent DNA 1000 chip to assess the yield and size distribution. As shown in FIG. 3, when a blocking oligo or gel size selection was not used to remove the ligation byproduct, >70% of the final library are amplified ligation byproducts. Byproduct runs at ~70 bp, desired miRNA products are ~90 bp. In contrast, as shown in FIG. 4, when a blocking oligonucleotide comprising 2'-O-methyl modifications was used only ~4% of the final library was amplified from ligation byproduct (~70 bp).

Figure 5:
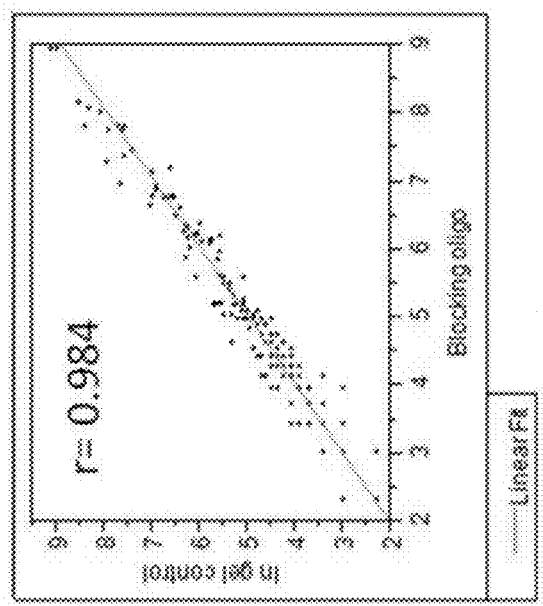
FIG. 5 Correlation between small RNA libraries generated using Ion total RNA-Seq with gel purification and using a blocking oligonucleotide.

Further, as shown in FIG. 5, when small RNA libraries generated using existing gel size selection protocol and RNA libraries prepared by the modified protocol using a blocking oligonucleotide were sequenced on PGM (Life Technologies) and mapped to miRBase 18 a strong correlation was observed. Counts from each miRNA were normalized and log transformed. A correlation coefficient of 0.984 was observed when comparing the two runs, indicating minimal bias was caused by using the blocking oligonucleotide method.

Example 5: Library Preparation Using A Blocking Oligonucleotide For Ion Total RNA-Seq Kit Adaptor Mix A blocking oligonucleotide was used for preparation of a sequencing library for use with the Ion Total RNA-Seq Kit. The level of miRNA in the sample was 2.2% as determined using an Agilent small RNA chip.

The sample was found to have an RIN of 8.8 as determined using Agilent® 2100 Bioanalyzer™ with RNA Nano chip as described above.

Using the Ion Total RNA-Seq Kit, 3 µL of the RNA sample was hybridized and ligated to the 5 and 3' adapters according to the manufacturer's directions. The sequence of the 5' adapter was:

5' GGCCAAGGCG 3'              (SEQ ID NO: 9)

3' CCGGTTCCGCNNNNNNN 5'       (SEQ ID NO: 10)
    where N can be any normal nucleotide.

The sequence of the 3' adapter was:

5' ATCACCGACTGCCCATAGAGAGG 3'    (SEQ ID NO: 3)

3' NNNNNNNTAGTGGCTGA 5'          (SEQ ID NO: 4)
    where N can be any normal nucleotide.

The ligated molecule was then reverse transcribed as described above using the RT primer:

5' CCTCTCTATGGGCAGTCG 3'    (SEQ ID NO: 6)

and the blocking oligonucleotide:

5' ATGGGCAGTCGGTIATCICCTTGGCC 3'    (SEQ ID NO: 11)

wherein nucleotides 1-13, 17, and 19-26 have 2'-O-methyl modifications, 14 and 18 are inosines, and the 3' terminal cytosine is further modified with an amine.

Purification of the resulting cDNA was performed using MAGMAX™ beads as described above. The purified cDNA was the amplified as described above using the following primers and thermocycler reaction times:

5' primer
                                    (SEQ ID NO: 12)
    CCATCTCATCCCTGCGTGTCTCCGACTCAGGGCCAAGGCG 3' primer
                                    (SEQ ID NO: 8)
    CCGCTTTCCTCTCTATGGGCAGTCGGTGAT

| Stage | Temp | Time |
| --- | --- | --- |
| Hold | 94° C. | 2 min |
| Cycle (2 Cycles) | 94° C. | 30 sec |
|  | 50° C. | 30 sec |
|  | 68° C. | 30 sec |
| Cycle (14 Cycles) | 94° C. | 30 sec |
|  | 62° C. | 30 sec |
|  | 68° C. | 30 sec |
| Hold | 68° C. | 5 min |

Amplified cDNA was purified using the MAGMAX™-96 total RNA isolation kit according to the manufacturer's instructions.

Assess the Yield and Size Distribution of the Amplified DNA

Figure 6:
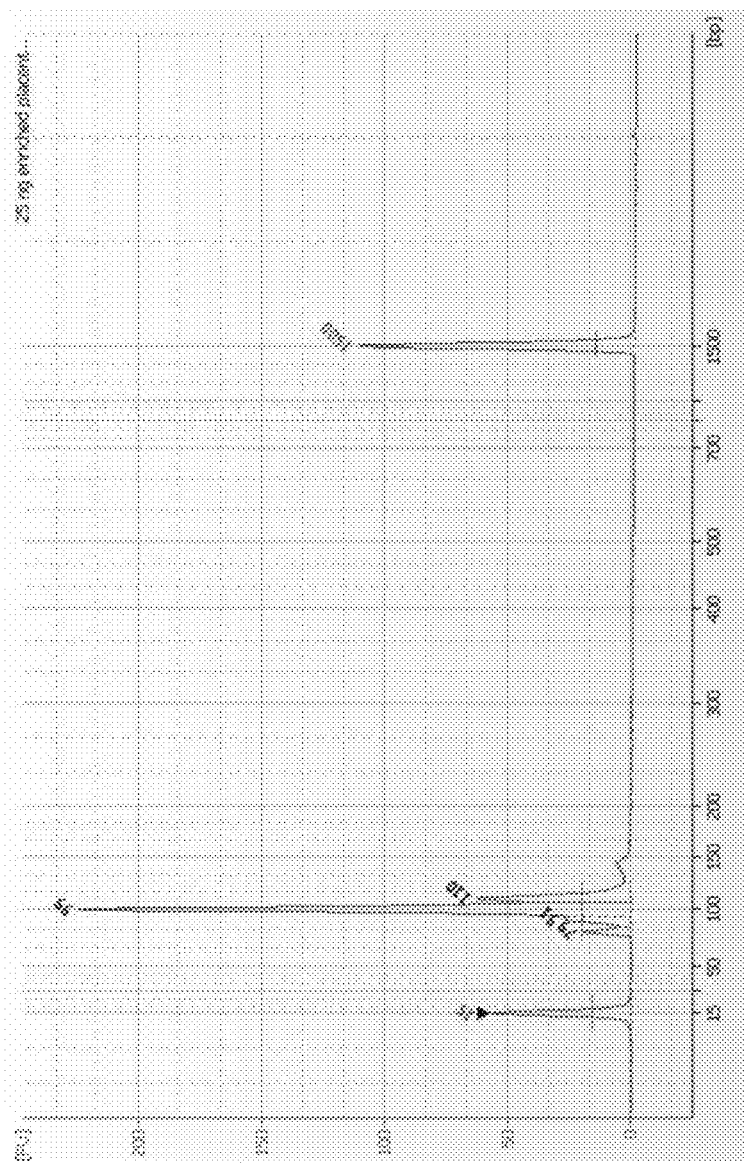
FIG. 6 Bioanalyzer trace for Small RNA library using a blocking oligonucleotide with 2'-O-methyl and inosine modifications.
Figure 7:
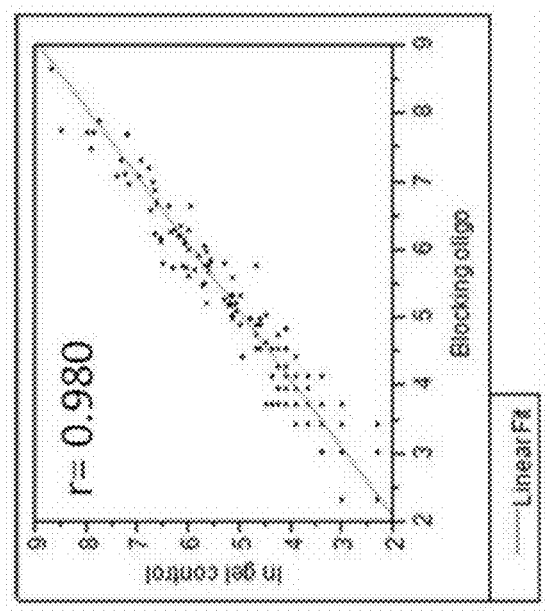
FIG. 7 Correlation between small RNA libraries generated using Ion Total RNA-Seq with gel purification and using a blocking oligonucleotide.

A 1 µL aliquot of the sample may be analyzed on an Agilent DNA 1000 chip to assess the yield and size distribution. As shown in FIG. 6, only ~4% of the final library was the result of amplification from the ligation byproduct (~79 bp). Further, as shown in FIG. 7, when small RNA libraries generated using existing gel size selection protocol and RNA libraries prepared by the modified protocol using a blocking oligonucleotide were sequenced and compared a correlation coefficient of 0.980 was observed, indicating minimal bias was caused by using the blocking oligonucleotide method.

Example 6: Library Preparation Using a Blocking Oligonucleotide for Ion Total RNA-Seq Kit Adaptor Mix A blocking oligonucleotide was used for preparation of a sequencing library for use with the Ion Total RNA-Seq Kit. The level of miRNA in the sample was 2.2% as determined using an Agilent small RNA chip.

The sample was found to have an RIN of 8.8 as determined using Agilent® 2100 Bioanalyzer™ with RNA Nano chip as described above.

Using the Ion Total RNA-Seq Kit, 3 μL of the RNA sample was hybridized and ligated to the 5 and 3' adapters according to the manufacturer's directions. The sequence of the 5' adapter was:

```
5' GGCCAAGGCG 3'          (SEQ ID NO: 9)

3' CCGGTTCCGCNNNNNNN 5'   (SEQ ID NO: 10)
where N can be any normal nucleotide.
```

The sequence of the 3' adapter was:

```
5' ATCACCGACTGCCCATAGAGAGG 3'   (SEQ ID NO: 3)

3' NNNNNNNTAGTGGCTGA 5'         (SEQ ID NO: 4)
where N can be any normal nucleotide.
```

The ligated molecule was then reverse transcribed as described above using the RT primer:

```
    CCTCTCTATGGGCAGTCG        (SEQ ID NO: 6)
``` and the blocking oligonucleotide:

```
5' GCAGTCGGTGATCGCCTTGGCC 3'   (SEQ ID NO: 13)
``` wherein nucleotides 1, 3, 5, 7, and 14, 16, 18, 20, 22 have LNA modifications and the 3' terminal cytosine is further modified with an amine.

Purification of the resulting cDNA was performed using MAGMAX™ beads as described above. The purified cDNA was the amplified as described above using the following primers and thermocycler reaction times:

```
5' primer
                                    (SEQ ID NO: 12)
CCATCTCATCCCTGCGTGTCTCCGACTCAGGGCCAAGGCG 3' primer
                                    (SEQ ID NO: 8)
CCGCTTTCCTCTCTATGGGCAGTCGGTGAT
```

| Stage | Temp | Time |
|---|---|---|
| Hold | 94° C. | 2 min |
| Cycle (2 Cycles) | 94° C. | 30 sec |

-continued

| Stage | Temp | Time |
|---|---|---|
| | 50° C. | 30 sec |
| | 68° C. | 30 sec |
| Cycle (14 Cycles) | 94° C. | 30 sec |
| | 62° C. | 30 sec |
| | 68° C. | 30 sec |
| Hold | 68° C. | 5 min |

Amplified cDNA was purified using the MAGMAX™-96 total RNA isolation kit according to the manufacturer's instructions.

Assess the Yield and Size Distribution of the Amplified DNA

Figure 8:
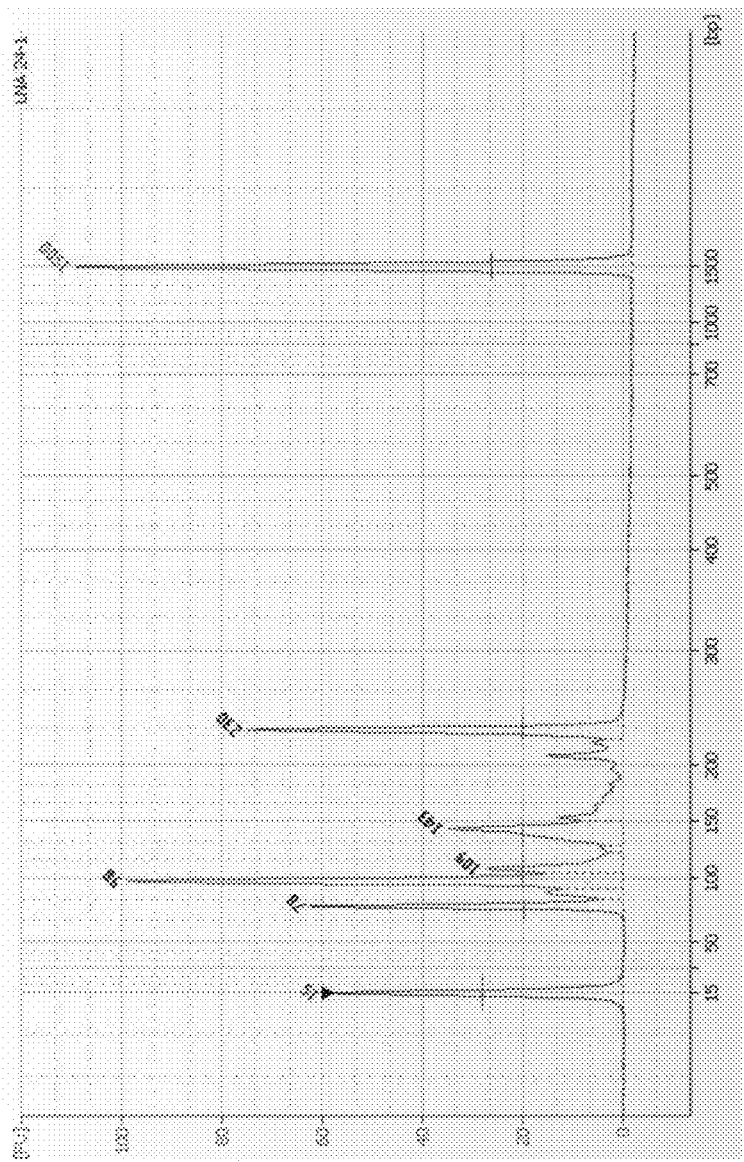
FIG. 8 Bioanalyzer trace for small RNA library using a blocking oligonucleotide comprising LNA.
Figure 9:
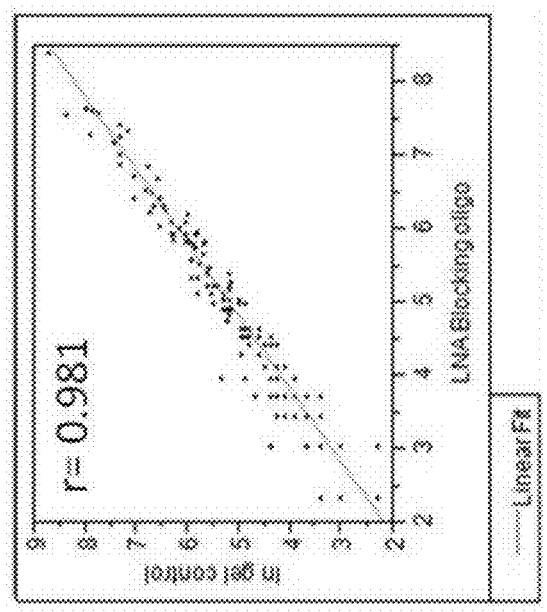
FIG. 9 Correlation between small RNA libraries generated using Ion Total RNA-Seq with gel purification and using a blocking oligonucleotide comprising LNA.

A 1 μL aliquot of the sample may be analyzed on an Agilent DNA 1000 chip to assess the yield and size distribution. As shown in FIG. 8, only 12.5% of the final library was amplified from the ligation byproduct (~78 bp). In addition, as shown in FIG. 9, when small RNA libraries generated using existing gel size selection protocol and RNA libraries prepared by the modified protocol using a blocking oligonucleotide were sequenced and compared, a correlation coefficient of 0.981 was observed, indicating minimal bias was caused by using the blocking oligonucleotide method.

Further exemplary embodiments are provided in the following numbered clauses.

1. An oligonucleotide comprising a first segment at a 5' prime end and a second segment at a 3' end, wherein the first segment hybridizes with a first nucleotide adapter molecule and the second segment hybridizes with a second nucleotide adapter molecule.

2. The oligonucleotide of clause 1, wherein the oligonucleotide is between 20 and 26 nucleotides in length 3. The oligonucleotide of clause 1, wherein the first segment is between 11 and 14 nucleotides in length.

4. The oligonucleotide of clause 1, wherein the second segment is between 9 and 12 nucleotides in length.

5. The oligonucleotide of clause 1, wherein the first segment comprises one or more modified nucleotides.

6. The oligonucleotide of clause 5, wherein the one or more modified nucleotides is a 2'-O-methyl nucleotide, or locked nucleic acid.

7. The oligonucleotide of clause 3, wherein the first segment comprises from 1 to 14 modified nucleotides.

8. The oligonucleotide of clause 3, wherein the first segment comprises from 1-7 indiscriminant nucleotides.

9. The oligonucleotide of clause 8, wherein the from 1-7 indiscriminant nucleotides are located within the first 7 bases from a 3' end of the second segment.

10. The oligonucleotide of clause 7, wherein the modified nucleotides are a 2'-O-methyl nucleotide or locked nucleic acid.

11. The oligonucleotide of clause 1, wherein the second segment is blocked at the 3' end.

12. A method for adding adapters to the ends of a plurality of a single stranded oligonucleotides comprising:
a) forming a mixture of the single stranded oligonucleotides with a double stranded 5' adapter having a 3' sticky end and a double stranded 3' adapter having a 5' sticky end,
b) adding an RNA ligase to the mixture under conditions such that the 5' adapter and the 3' adapter are ligated to the ends of the plurality of single stranded oligonucleotides,
c) denaturing oligonucleotides present in step (b) and adding and an oligonucleotide of clause 1 under conditions such that the oligonucleotide of clause 1 binds to an artifact of the ligation reaction formed by the 5' adapter and the 3' adapter being ligated to each other such that reverse transcription of the artifact is blocked.

13. The method of clause 12, wherein the oligonucleotide of clause 1 is between 20 and 26 nucleotides in length.

14. The method of clause 12, wherein the first segment of the oligonucleotide of clause 1 is between 11 and 14 nucleotides in length.

15. The method of clause 12, wherein the second segment of the oligonucleotide of clause 1 is between 9 and 12 nucleotides in length.

16. The method of clause 12, wherein the first segment of the oligonucleotide of clause 1 comprises one or more modified nucleotides.

17. The method of clause 16, wherein the one or more modified nucleotides is a 2'-O-methyl nucleotide, or locked nucleic acid.

18. The method of clause 14, wherein the first segment of the oligonucleotide of clause 1 comprises from 1 to 14 modified nucleotides.

19. The method of clause 14, wherein the first segment of the oligonucleotide of clause 1 comprises from 1-7 indiscriminant nucleotides.

20. The method of clause 19, wherein the from 1-7 indiscriminant nucleotides are located within the first 7 bases from a 3' end of the second segment.

21. The method of clause 18, wherein the modified nucleotides are a 2'-O-methyl nucleotide or locked nucleic acid.

22. The method of clause 12, wherein the second segment of the oligonucleotide of clause 1 is blocked at the 3' end.

All publications, patents and patent applications mentioned in this Specification are indicative of the level of skill of those of ordinary skill in the art and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one of ordinary skill in the art are intended to be included within the scope of the following claims.

What is claimed:

1. A composition comprising a blocking oligonucleotide wherein the blocking oligonucleotide comprises:
   (1) a first segment of consecutive nucleotides that hybridizes to a first adapter, wherein the first adapter comprises a sequence of nucleotides complementary to a primer for a reverse transcriptase or polymerase, and
   (2) a second segment of consecutive nucleotides located 3' of the first segment that hybridizes to a second adapter, wherein the second adapter comprises a priming sequence for a polymerase;
   wherein the first segment comprises one or more indiscriminate nucleotides located within the last 7 nucleotides at the 3' end of the first segment and/or wherein the second segment comprises one or more indiscriminate nucleotides within the first 7 nucleotides at the 5' end of the second segment; and
   wherein the blocking oligonucleotide specifically hybridizes to and binds the junction of a nucleic acid adapter:adapter byproduct containing the first and second adapters, wherein the blocking oligonucleotide binds the 3' end of the 5' adapter of the byproduct and binds the 5' end of the 3' adapter of the byproduct such that the adapter:adapter byproduct cannot be used to generate a cDNA by a reverse transcriptase.

2. The composition of claim 1, wherein the $t_m$ of hybridization of the 3' end of the first segment to the 5' end of the first adapter is lower than the $t_m$ of hybridization of the remainder of the blocking oligonucleotide to the adapter:adapter product molecule.

3. The composition of claim 1, wherein the indiscriminate nucleotides are selected from the group consisting of 2'-deoxyinosine and hydrophobic aromatic non-hydrogen bonding bases.

4. The composition of claim 1, wherein the first and/or second segment comprises one or more modified nucleotides.

5. The composition of claim 4, wherein the one or more modified nucleotides is selected from the group consisting of a 2'-O-methyl modified nucleotide, a 2'-deoxy-2'-fluoro modified nucleotide, a 2'-deoxy-modified nucleotide, a 2'-alkyl-modified nucleotide, a locked nucleotide, a nucleotide having a 5'-phosphorothioate group, an abasic nucleotide, a 2'-amino-modified nucleotide, a morpholino nucleotide, and a phosphoramidate nucleotide.

6. The composition of claim 1, wherein the first and/or second segment comprises between 1 and 12 modified nucleotides.

7. The composition of claim 1, wherein the blocking oligonucleotide comprises the nucleotide sequence according to SEQ ID NO: 11.

8. The composition of claim 1, further comprising a reverse transcription enzyme.

9. The composition of claim 1, wherein the 3' terminal end of the blocking oligonucleotide comprises a blocking moiety that blocks primer extension or reverse transcription.

10. The composition of claim 9, wherein the blocking moiety at the 3' terminal end of the blocking oligonucleotide comprises an amine group, a C3 amino group, a C6 amino group, a thiol group or a di-deoxynucleotide.

11. The composition of claim 1, wherein the blocking oligonucleotide is between 20 and 26 nucleotides in length.

12. The composition of claim 1, wherein the first segment is between 11 and 14 nucleotides in length.

13. The composition of claim 1, wherein the second segment is between 9 and 12 nucleotides in length.

14. The composition of claim 1, wherein the first segment is between 11 and 14 nucleotides in length and the second segment is between 9 and 12 nucleotides in length.

15. The composition of claim 1, wherein the blocking oligonucleotide is hybridized to an adapter-adapter product, and wherein the adapter-adapter product comprises a single-stranded nucleic acid molecule having one strand of the first adapter joined to one strand of the second adapter.

16. The composition of claim 15, wherein the adapter:adapter product comprises one strand of RNA joined to one strand of DNA.

17. The composition of claim 1, further comprising a reverse transcriptase.

18. The composition of claim 1, further comprising a plurality of single-stranded nucleic acids comprising a strand of the first adapter ligated to the 3' end of the nucleic acid and a strand of the second adapter ligated to the 5' end of the nucleic acid.

* * * * *